United States Patent [19]
Sui et al.

[11] Patent Number: 6,077,841
[45] Date of Patent: Jun. 20, 2000

[54] 5-HETEROCYCLYL PYRAZOLO[4,3-D] PYRIMIDIN-7-ONES FOR THE TREATMENT OF MALE ERECTILE DYSFUNCTION

[75] Inventors: Zhihua Sui, Flemington; Jihua Guan, Raritan; Mark J. Macielag, Branchburg, all of N.J.

[73] Assignee: Janssen Pharmaceutica, N.V., Beerse, Belgium

[21] Appl. No.: 09/388,851

[22] Filed: Sep. 2, 1999

Related U.S. Application Data

[60] Provisional application No. 60/099,268, Sep. 4, 1998.
[51] Int. Cl.$^7$ .................. A61K 31/519; C07D 487/04
[52] U.S. Cl. .................. 514/234.2; 544/118; 544/262
[58] Field of Search .................. 544/118, 262; 514/258, 234.2

[56] References Cited

U.S. PATENT DOCUMENTS

| | | | |
|---|---|---|---|
| 4,666,908 | 5/1987 | Hamilton | 514/229 |
| 5,250,534 | 10/1993 | Bell et al. | 514/258 |
| 5,294,612 | 3/1994 | Bacon et al. | 514/234.2 |
| 5,346,901 | 9/1994 | Bell et al. | 514/258 |

FOREIGN PATENT DOCUMENTS

| | | |
|---|---|---|
| 0 636 626 A1 | 1/1995 | European Pat. Off. . |
| 0 812 845 B1 | 12/1997 | European Pat. Off. . |
| 61-236778 | 1/1986 | Japan . |
| WO 94/28902 | 12/1994 | WIPO . |
| WO 96/16644 | 6/1996 | WIPO . |
| WO 96/16657 | 6/1996 | WIPO . |

OTHER PUBLICATIONS

J. Org. Chem. vol. 40 No. 19; Tam Huynh–Dinh, annie Kolb, Catherine Gouyette and Jean Igolen; Synthesis of C Nucleosides.X1 Structural Analogs of Formycin B; pp. 2825–2830 (1975).

J. Med. Chem; Harriet W. Hamilton Daniel F. Ortwine, Donald F. Worth, and James A. Bristol; Synthesis and Structure—Activity Relatioships of Pyrazolo[4,3–d] pyrimidin–7–One as Adenosine Receptor Antagonists; vol. 30; pp. 91–96 (1987).

J. Med. Chem.; C. Subramanyam et al; 6–(4–Pyridinyl)–H–1,2,3–Triazolo{4,5–D]–Pyrimidin–4 (5h)—One: A Structurally Novel Competitive AMPA Receptor Antagonist; vol. 38; pp. 587–589 (1995).

*Primary Examiner*—Mukund J. Shah
*Assistant Examiner*—Sudhaker B. Patel
*Attorney, Agent, or Firm*—Mary Appollina

[57] ABSTRACT

The invention is directed to novel substituted 5-heterocyclyl pyrazolopyrimidinones and derivatives thereof, their synthesis and their use in treating sexual dysfunction in mammals, especially male erectile dysfunction. Pharmaceutical compositions containing the compounds and methods of using them to treat sexual dysfunction are also described.

15 Claims, No Drawings

5-HETEROCYCLYL PYRAZOLO[4,3-D] PYRIMIDIN-7-ONES FOR THE TREATMENT OF MALE ERECTILE DYSFUNCTION

CROSS-REFERENCE TO RELATED APPLICATION

This application claims priority from United States provisional application Ser. No. 60/099,268, filed Sep. 4, 1998, the contents of which are hereby incorporated by reference.

FIELD OF THE INVENTION

This invention relates to certain novel compounds, their synthesis and their use for the treatment of male erectile dysfunction. More particularly, the compounds of the present invention are substituted 5-heterocyclyl pyrazolopyrimidinones useful for the treatment of male erectile dysfunction.

BACKGROUND OF THE INVENTION

Erectile dysfunction (ED) is defined as the inability to achieve or maintain an erection sufficiently rigid for satisfactory sexual intercourse. Currently it is estimated that approximately 7–8% of the male population suffer from some degree of ED, the equivalent of at least 20 million men in the United States alone. Since the likelihood of ED increases with age, it is projected that the incidence of this condition will rise in the future as the average age of the population increases.

Male erectile dysfunction may be the consequence of psychogenic and/or organic factors. Although ED is multifactorial, certain sub-groups within the male population are more likely to present with the symptoms of the disorder. In particular, patients with diabetes, hypertension, heart disease, and multiple sclerosis have a particularly high prevalence of ED. In addition, patients who take certain classes of drugs such as antihypertensives, antidepressants, sedatives, and anxiolytics are more prone to suffer from ED.

Treatments for ED include a variety of pharmacologic agents, vacuum devices, and penile prostheses. Among the pharmacologic agents, papaverine, phentolamine, and alprostadil are currently used in practice. These agents are only effective after direct intracavernosal or intraurethral injection, and are associated with side effects such as priapism, fibrosis, penile pain and hematoma at the injection site. Vacuum devices are a noninasive alternative treatment for ED. These devices produce an erection by creating a negative pressure around the shaft of the penis resulting in an increased blood flow into the corpus cavernosum via passive arterial dilation. Although this form of therapy is frequently successful in ED of organic origin, complaints include the lack of spontaneity and the time involved in using a mechanical device, and difficulty and discomfort with ejaculation. A variety of semi-rigid or inflatable penile prostheses have been used with some success, particularly in diabetic men. These devices are generally considered when other treatment options have failed, and are associated with an increased risk of infection and ischemia.

Recently, the phosphodiesterase V (PDEV) inhibitor, sildenafil (Viagra®) was approved by the FDA as an orally effective medication for the treatment of ED. Sildenafil, 5-[2-ethoxy-5-(4-methylpiperazin-1-ylsulphonyl)phenyl]-1-methyl-3-n-propyl-6,7-dihydro-1H-pyrazolo[4,3-d]pyrimidin-7-one and a number of related analogs and their use as antianginal agents are described in U.S. Pat. Nos. 5,250,534 and 5,346,901. The use of sildenafil and related analogs for treating male erectile dysfuntion is described in PCT International Application Publication No. WO 94/28902, published Dec. 22, 1994. In clinical studies, the drug improved sexual function in about 70% of the men who suffer from ED of psychogenic or organic etiology. However, the drug showed less dramatic efficacy in patients who had undergone a radical prostatectomy, with improved erections in 43% of patients who took sildenafil versus 15% on placebo. In addition, the use of sildenafil is associated with several undesirable side effects including headache, flushing and disrupted color vision which result from non-selective effects on a variety of tissues. In spite of these shortcomings, the drug is viewed by patients as preferable to other treatments which involve the introduction of medication directly into the penis via injection, the use of an external device or a surgical procedure.

Dinh et al. (*J. Org. Chem.* 1975, 40, 2825) describe the preparation of 5-hydroxymethyl-2-furanyl and 5-benzyloxy-2-furanyl pyrazolo[4,3-d]pyrimidin-7-ones as by-products and intermediates in the preparation of analogs of formycin B.

Bacon et al., in U.S. Pat. No. 5,294,612, describe a series of 6-heterocyclyl pyrazolo[3,4-d]pyrimidin-4-one phosphodiesterase inhibitors and their use in treating cardiovascular disease.

Sexually stimulated penile erection results from a complex interplay of physiological processes involving the central nervous system, the peripheral nervous system, and the smooth muscle. Specifically, release of nitric oxide from the non-adrenergic, non-cholinergic nerves and endothelium activates guanylyl cyclase and increases intracellular cGMP levels within the corpus cavernosum. The increase in intracellular cGMP reduces intracellular calcium levels, resulting in trabecular smooth muscle relaxation, which, in turn, results in corporal volume expansion and compression of the sub-tunical venules leading to penile erection.

Agents that increase the concentration of cGMP in penile tissue, either through enhanced release or reduced breakdown of cGMP, are expected to be effective treatments for ED. The intracellular levels of cGMP are regulated by the enzymes involved in its formation and degradation, namely the guanylate cyclases and the cyclic nucleotide phosphodiesterases (PDEs). To date, at least nine families of mammalian PDEs have been described, five of which are capable of hydrolyzing the active, cGMP, to the inactive, GMP, under physiological conditions (PDEs I, II, V, VI, and IX). PDE V is the predominant isoform in human corpus cavernosum. Inhibitors of PDEV, therefore, would be expected to increase the concentration of cGMP in the corpus cavernosum and enhance the duration and frequency of penile erection.

PDEV also has been found in human platelets and vascular smooth muscle, suggesting a role for this enzyme in the regulation of intracellular concentrations of cGMP in cardiovascular tissue. In fact, inhibitors of PDEV have been shown to produce endothelial-dependent vasorelaxation by potentiating the increases in intracellular cGMP induced by nitric oxide. Moreover, PDEV inhibitors selectively lower the pulmonary arterial pressure in animal models of congestive heart failure and pulmonary hypertension. Hence in addition to their utility in ED, PDEV inhibitors would likely be of therapeutic benefit in conditions like heart failure, pulmonary hypertension, and angina.

Accordingly, it is an object of the invention to identify compounds which inhibit phosphodiesterases, specifically PDEV. It is another object of the invention to identify compounds which are useful for the treatment of sexual dysfunction, particularly erectile dysfunction in male animals. Still another object of the invention is to identify methods for treating sexual dysfunction, especially erectile dysfunction, using the compounds of the present invention.

We now describe a series of 5-heterocyclyl-pyrazolyl[4,3-d]pyrimidin-7-ones with the ability to inhibit phosphodiesterase type 5 in an enzyme assay.

SUMMARY OF THE INVENTION

The present invention is directed to a compound of formula (I)

(I)

wherein
$R^1$ and $R^2$ are each independently selected from hydrogen or $C_1$–$C_6$ alkyl;
$R^3$ is selected from or is a five membered heteroaromatic ring which consists of carbon atoms and from one to three heteroatoms selected from N, O or S;
$R^4$, $R^5$, $R^6$ and $R^7$ are each independently selected from hydrogen, $C_1$–$C_6$ alkyl, fluorinated $C_1$–$C_6$ alkyl, cyano, (hydroxy)$C_1$–$C_6$ alkyl, $C_1$–$C_6$ alkoxy, fluorinated $C_1$–$C_6$ alkoxy, $C_1$–$C_6$ alkanoyl, halogen, hydroxy, $C_1$–$C_6$ alkyl-NR$^8$R$^9$, NR$^8$R$^9$, CONR$^8$R$^9$ or SO$_2$NR$^8$R$^9$;
$R^8$ is selected from hydrogen or $C_1$–$C_6$ alkyl,
$R^9$ is selected from hydrogen, $C_1$–$C_6$ alkyl, or $C_1$–$C_6$ alkyl-NR$^{13}$R$^{14}$, or
$R^8$ and $R^9$ together with the nitrogen to which they are attached form an unsubstituted or substituted pyrrolidinyl, piperidinyl, morpholinyl or 4-N(R$^{10}$)-piperazinyl group wherein the substituent is selected from $C_1$–$C_6$ alkyl, $C_1$–$C_6$ alkoxy, NR$^{11}$R$^{12}$ or CONR$^{11}$R$^{12}$;
$R^{10}$ is selected from hydrogen, $C_1$–$C_6$ alkyl, $C_3$–$C_6$ cycloalkyl, (hydroxy)$C_1$–$C_6$ alkyl, aryl, heteroaryl, aralkyl, aralkenyl or C(O)NH2; preferably, $R^{10}$ is selected from hydrogen, $C_1$–$C_6$ alkyl, (hydroxy)$C_1$–$C_6$ alkyl, aryl, heteroaryl, aralkyl, aralkenyl or C(O)NH2;
$R^{11}$ and $R^{12}$ are each independently selected from hydrogen, $C_1$–$C_6$ alkyl, (hydroxy)$C_1$–$C_6$ alkyl or ($C_1$–$C_6$ alkoxy)$C_1$–$C_6$ alkyl; and
$R^{13}$ and $R^{14}$ are each independently selected from hydrogen or $C_1$–$C_6$ alkyl, or $R^{13}$ and $R^{14}$ together with the nitrogen to which they are attached form an unsubstituted or substituted pyrrolidinyl, piperidinyl or morpholinyl group wherein the substituent is selected from $C_1$–$C_6$ alkyl, $C_1$–$C_6$ alkoxy, NR$^{11}$R$^{12}$ or CONR$^{11}$R$^{12}$;
provided that when $R^3$ is and $R^5$ and $R^6$ are both hydrogen, then $R^4$ is selected from hydrogen, $C_1$–$C_6$ alkyl, fluorinated $C_1$–$C_6$ alkyl, cyano, (hydroxy)$C_2$–$C_6$ alkyl, $C_1$–$C_6$ alkoxy, fluorinated $C_1$–$C_6$ alkoxy, $C_1$–$C_6$ alkanoyl, halogen, hydroxy, $C_1$–$C_6$ alkyl-NR$^8$R$^9$, NR$^8$R$^9$, CONR$^8$R$^9$ or SO$_2$NR$^8$R$^9$;
and pharmaceutically acceptable salts thereof.

In one embodiment of the invention is the compound of formula (I) wherein
$R^1$ and $R^2$ are each independently selected from hydrogen and $C_1$–$C_4$ alkyl;
$R^3$ is selected from or

;

is a five membered heteroaromatic ring selected from pyrrolyl, furanyl, thienyl, or imidazolyl;
$R^4$ and $R^6$ are each independently selected from hydrogen, $C_1$–$C_4$ alkyl, fluorinated $C_1$–$C_4$ alkyl, cyano, (hydroxy)$C_1$–$C_4$ alkyl, $C_1$–$C_4$ alkoxy, fluorinated $C_1$–$C_4$ alkoxy, $C_1$–$C_4$ alkanoyl, halogen, hydroxy, $C_1$–$C_4$ alkyl-NR$^8$R$^9$, NR$^8$R$^9$, CONR$^8$R$^9$ or SO$_2$NR$^8$R$^9$;
$R^5$ is selected from hydrogen, $C_1$–$C_4$ alkyl or $C_1$–$C_4$ alkoxy;
$R^8$ is selected from hydrogen or $C_1$–$C_4$ alkyl,
$R^9$ is selected from hydrogen, $C_1$–$C_4$ alkyl, or $C_1$–$C_4$ alkyl-NR$^{13}$R$^{14}$, or
$R^8$ and $R^9$ together with the nitrogen to which they are attached form an unsubstituted or substituted pyrrolidinyl, piperidinyl, morpholinyl or 4-N(R$^{10}$)-piperazinyl group wherein the substituent is selected from $C_1$–$C_4$ alkyl, $C_1$–$C_4$ alkoxy, NR$^{11}$R$^{12}$ or CONR$^{11}$R$^{12}$;

$R^{10}$ is selected from hydrogen, $C_1$–$C_4$ alkyl, (hydroxy) $C_1$–$C_4$ alkyl, aryl, heteroaryl, ar($C_1$–$C_4$)alkyl, ar($C_1$–$C_4$)alkenyl or $C(O)NH_2$;

provided that when $R^3$ is

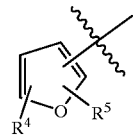

and $R^5$ is hydrogen, then $R^4$ is selected from hydrogen, $C_1$–$C_4$ alkyl, fluorinated $C_1$–$C_4$ alkyl, cyano, (hydroxy) $C_2$–$C_4$ alkyl, $C_1$–$C_4$ alkoxy, fluorinated $C_1$–$C_4$ alkoxy, $C_1$–$C_4$ alkanoyl, halogen, hydroxy, $C_1$–$C_4$ alkyl-$NR^8R^9$, $NR^8R^9$, $CONR^8R^9$ or $SO_2NR^8R^9$;

and all other variables are as defined above;

and pharmaceutically acceptable salts thereof.

In a class of the invention is the compound of formula (I) selected from

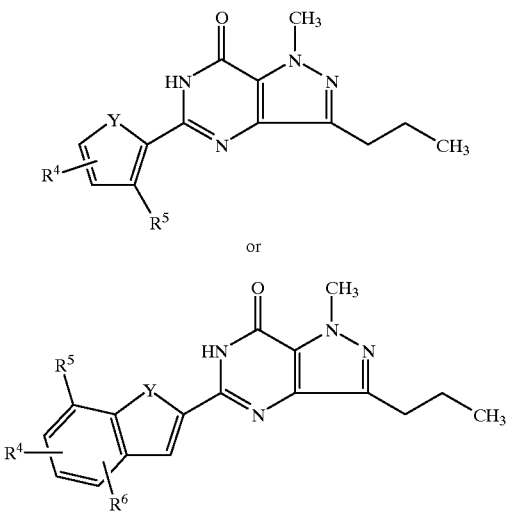

wherein Y is selected from O, S or N—$R^{15}$ where $R^{15}$ is selected from hydrogen and $C_1$–$C_4$ alkyl;

and all other variables are as defined above;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating sexual dysfunction, especially male erectile dyfunction, and/or impotence in a subject in need thereof comprising administering to the subject a therapeutically effective amount of any of the compounds or pharmaceutical compositions described above.

An example of the invention is a method for increasing the concentration of cGMP in penile tissue through the inhibition of phosphodiesterases, specifically PDEV, in a male subject in need thereof comprising administering to the subject an effective amount of any of the compounds or pharmaceutical compositions described above.

Further illustrating the invention is a method of treating a condition selected from the group consisting of heart failure, pulmonary hypertension, and angina in a subject in need thereof comprising administering to the subject a therapeutically effective amount of any of the compounds or pharmaceutical compositions described above.

Further exemplifying the invention is a method of producing endothelial-dependent vasorelaxation by potentiating the increases in intracellular cGMP induced by nitric oxide in a subject in need thereof comprising administering to the subject an effective amount of any of the compounds or pharmaceutical compositions described above.

Another example of the invention is the use of any of the compounds described above in the preparation of a medicament for: (a) treating sexual dysfunction, especially male erectile dyfunction, (b) treating impotence, (c) increasing the concentration of cGMP in penile tissue through the inhibition of phosphodiesterases, specifically PDEV, and/or (d) treating a condition selected from the group consisting of heart failure, pulmonary hypertension, and angina, in a subject in need thereof.

DETAILED DESCRIPTION OF THE INVENTION

The present invention provides substituted 5-heterocyclyl pyrazolopyrimidinones useful for the treatment of sexual dysfunction, especially ED. Although the compounds of the present invention are useful primarily for the treatment of male sexual dysfunction or erectile dysfunction, they may also be useful for the treatment of female sexual dysfunction related to clitoral disturbances, and of premature labor and dysmenorrhea.

More particularly, the compounds of the present invention are of the formula I

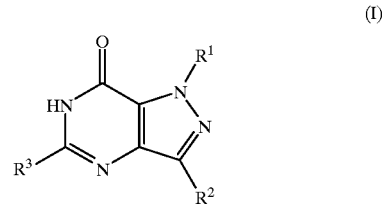

(I)

wherein all variables are as defined above.

The compounds of formula I may exist in tautomeric equilibrium with the corresponding enol form as compounds of formula (VII):

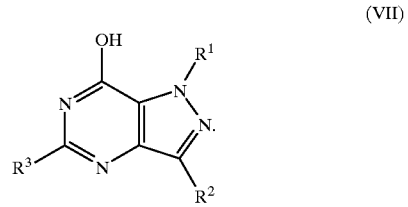

(VII)

While the compounds are believed to exist predominantly in the keto form as compounds of formula (I) and will be represented as such throughout this specification, it should be understood that the invention contemplates both tautomeric forms, as well as mixtures thereof, and that all such forms and mixtures thereof are included within the scope of the present invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "alkyl" shall mean straight or branched chain alkanes of one to six carbon atoms, or any number within this range. For example, alkyl radicals include, methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Similarly, alkenyl and alkynyl groups include straight and branched chain alkenes and alkynes having 1 to 8 carbon atoms, or any number within this range.

The term "aryl" indicates aromatic groups such as phenyl and naphthyl.

The term "aralkyl" means a $C_1$–$C_6$ alkyl group substituted with an aryl group (e.g., benzyl, phenylethyl). Similarly, the term "aralkenyl" means a $C_1$–$C_6$ alkenyl group substituted with an aryl group The term "halogen" shall include iodine, bromine, chlorine and fluorine.

The symbol

and the term "five membered heteroaromatic ring", as used herein, represent a stable five membered monocyclic aromatic ring system which consists of carbon atoms and from one to three heteroatoms selected from N, O or S. The heteroaromatic ring may be attached at any heteroatom or carbon atom which results in the creation of a stable structure. Moreover, when the heteroaromatic ring is substituted, e.g., by $R^4$, $R^5$ or $R^6$ substituents, the substituent(s) may be attached at any carbon atom or heteroatom within the ring which results in the creation of a stable structure. Examples of five membered heteroaromatic rings include, but are not limited to, furanyl, imidazolyl, isoxazolyl, oxazolyl, pyrazolyl, pyrrolyl, thienyl, thiazolyl, thiadiazolyl and triazolyl.

The symbol

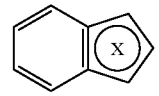

represents a nine membered benzo-fused heteroaromatic ring system which consists of carbon atoms and from one to three heteroatoms selected from N, O or S. The benzo-fused heteroaromatic ring may be attached at any heteroatom or carbon atom which results in the creation of a stable structure. Moreover, when the benzo-fused heteroaromatic ring is substituted, e.g., by $R^4$, $R^5$, $R^6$ or $R^7$ substituents, the substituent(s) may be attached at any carbon atom or heteroatom within the ring which results in the creation of a stable structure. Examples of nine membered benzo-fused heteroaromatic rings include, but are not limited to, benzimidazolyl, benzofuranyl, benzothienyl, benzisoxazolyl, benzoxazolyl, indazolyl, indolyl, benzothiazolyl, benzothiadiazolyl and benzotriazolyl.

The term "heteroaryl" as used herein represents a stable five or six membered monocyclic aromatic ring system or a nine or ten membered benzo-fused heteroaromatic ring system which consists of carbon atoms and from one to three heteroatoms selected from N, O or S. The heteroaryl group may be attached at any heteroatom or carbon atom which results in the creation of a stable structure. Examples of heteroaryl groups include, but are not limited to pyridyl, pyrimidinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, indazolyl, indolyl, benzothiazolyl, benzothiadiazolyl, benzotriazolyl, quinolinyl or isoquinolinyl. Preferred heteroaryl groups include pyridyl, pyrimidinyl, thiazolyl, imidazolyl, benzimidazolyl, quinolinyl and isoquinolinyl.

Under standard nomenclature used throughout this disclosure, the terminal portion of the designated side chain is described first, followed by the adjacent functionality toward the point of attachment. Thus, for example, a "phenylC$_1$–C$_6$ alkylamidoC$_1$–C$_6$alkyl" substituent refers to a group of the formula:

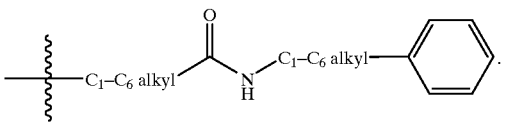

As used herein, the term "composition" is intended to encompass a product comprising the specified ingredients in the specified amounts, as well as any product which results, directly or indirectly, from combinations of the specified ingredients in the specified amounts.

It is intended that the definition of any substituent or variable (e.g., R$^{10}$ in claim 3) at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The utility of the compounds to treat ED can be determined according to the procedure described in Example 4 herein. Additionally, methods for determining the cGMP PDE and cAMP PDE inhibitory activities of the compounds, which are indicative of their utility for treating ED, are described in WO 93106104, WO 93/07149, WO 93/12095, WO 94100453, WO 94/05661, and WO 96/16657.

The present invention therefore provides a method of treating erectile dysfunction in a subject in need thereof which comprises administering any of the compounds as defined herein in a quantity effective to treat ED. The compound may be administered to a patient by any conventional route of administration, including, but not limited to, intravenous, oral, subcutaneous, intramuscular, intradermal and parenteral. The quantity of the compound which is effective for treating ED is between 0.1 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating ED described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of ED is required.

The daily dosage of the products may be varied over a wide range from 5 to 1,000 mg per adult human per day. For oral administration, the compositions are preferably provided in the form of tablets containing, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.1 mg/kg to about 20 mg/kg of body weight per day. Preferably, the range is from about 0.2 mg/kg to about 10 mglkg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

Abbreviations used in the specification, particularly the Schemes and Examples, are as follows:
DMAP=dimethylaminopyridine
DMF=dimethylformamide
DMSO=dimethylsulfoxide
Et$_3$N=triethylamine
EtOH=ethanol
MeOH=methanol
r.t.=room temperature
TEA=triethylamine The compounds of the invention may be prepared by the reaction of a compound of the general formula (II):

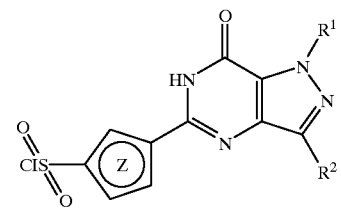

where $R^1$ and $R^2$ are as previously defined, and

is a suitably substituted five membered heteroaromatic ring or a suitably substituted nine membered benzo-fused heteroaromatic ring as defined for $R^3$ above, with a suitably substituted amine as defined for $R^8$ and $R^9$ above. The reaction is generally carried out a room temperature, preferably in the presence of a solvent, for example an alkanol containing one to three carbon atoms, using an excess of the amine to scavenge the acid by-product, HCl.

Compounds of the general formula (II) may be prepared from compounds of the general formula (III):

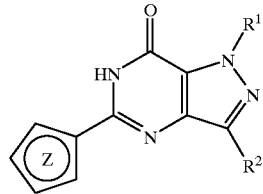

III by reacting with chlorosulfonic acid at temperatures ranging from −20° C. to 50° C. depending on the reactivity of the heterocyclic moiety,

Compounds of general formula (III) may be prepared from compounds of the general formula (IV):

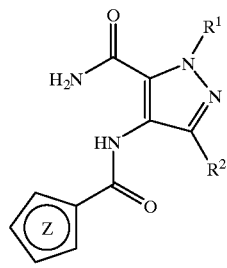

IV by the application of known cyclization methods for pyrimidinone ring formation. Thus, for example, the cyclization may be effected by the treatment of (IV) with a base such as sodium hydroxide or potassium carbonate in an ethanol-water medium at reflux temperature for 2–65 hours. Alternatively, compounds of the general formula (III) may also be obtained by treatment of (IV) with polyphosphoric acid at or near 140° C. for 6–18 hours.

Compounds of the general formula (IV) may be prepared from compounds of the general formula (V):

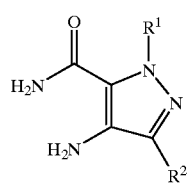

V by reaction with a compound of general formula (VI):

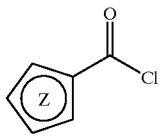

VI wherein

is as previously defined. The reaction is generally carried out using an excess of (VI) in the presence of an excess of an aliphatic tertiary amine such as triethylamine to act as scavenger for the acid by-product (HCl), optionally in the presence of a catalyst such as 4-dimethylaminopyridine, in an inert solvent such as dichloromethane at 0° C. to room temperature for 2–24 hours.

The amines used in the reaction with (II) to form the compounds of the invention, the aminopyrazoles of formula (V), and the acyl chlorides of formula (VI), when not commercially available, can be readily obtained by one of ordinary skill in the art by conventional synthetic procedures, in accordance with literature precedent, from readily accessible starting materials using standard reagents and reaction conditions.

As a further illustration of the synthesis of the compounds of the invention, the preparation of 5-[3-ethoxy-5-(4-methylpiperazinylsulfonyl)thiophene-2-yl)-1-methyl-3-n-propyl-6,7-dihydro-1H-pyrazolo-[4,3-d]pyrimidin-7-one and 5-[3-hydroxy-5-(4-methylpiperazinylsulfonyl) thiophene-2-yl)-1-methyl-3-n-propyl-6,7-dihydro-1 H-pyrazolo-[4,3-d]pyrimidin-7-one is detailed in Scheme I. Thus, the starting material, pyrazole 1 was reacted with the thiophenecarbonyl chloride 2 to give the intermediate 3. The cyclization of 3 was effected with sodium hydroxide in ethanol to give 4. Chlorosulfonylation followed by reaction with N-methylpiperazine gave compound 5 and compound 6.

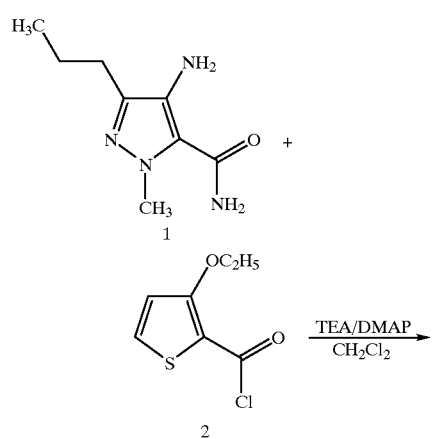

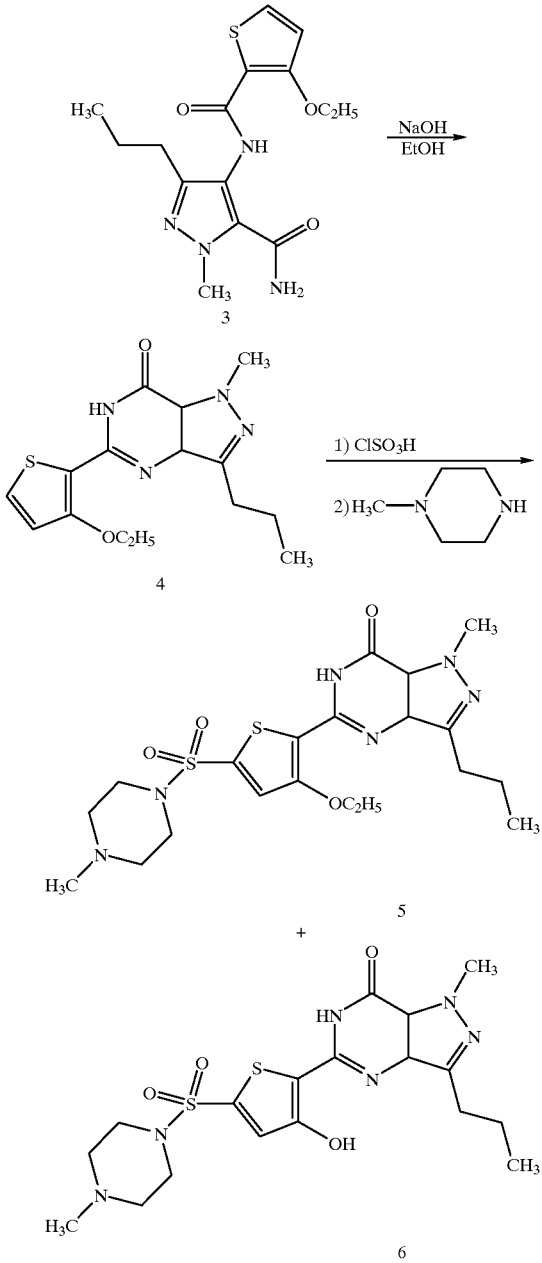

Scheme I

The following Examples are set forth to aid in the understanding of the invention, and are not intended and should not be construed to limit in any way the invention set forth in the claims which follow thereafter.

Unless otherwise indicated, $^1$H NMRs were run on a 300 MHz Bruker AC 300 instrument.

EXAMPLE 1

5-[3-Ethoxy-5-(4-methylpiperazinylsulfonyl) thiophene-2-yl)-1-methyl-3-n-propyl-6,7-dihydro-1H-pyrazolo-[4,3-d]pyrimidin-7-one (5) and 5-[3-hydroxy-5-(4-methylpiperazinylsulfonyl)thiophene-2-yl]-1-methyl-3-n-propyl-6,7-dihydro-1H-pyrazolo-[4,3-d]pyrlmidin-7-one (6)

a. 4-(3-Ethoxythiophene-2-carboxamido)-1-methyl-3-n-propylpyrazole-5-carboxamide (3)

3-Ethoxythiophene-2-carbonyl chloride 2, prepared from the reaction of 3-ethoxythiophene-2-carboxylic acid (2.79 g, 16.2 mmol) with oxalyl chloride, was added to a solution of 4-amino-1-methyl-3-n-propylpyrazole-5-carboxamide 1 (2.08 g, 11.4 mmol), DMAP (28 mg, 0.23 mmol) and Et$_3$N (1.64 g, 16.2 mmol) in anhydrous CH$_2$Cl$_2$ (30 mL) at 0° C., and stirred at r.t. for 24 h. The mixture was washed with 1 N HCl and dried with MgSO$_4$. Chromatography (silica gel, hexane:ethyl acetate=3:1) gave a white solid; mp: 103–104° C.; $^1$H NMR (DMSO-d$_6$) δ 0.87 (t, J=7 Hz, 3 H), 1.39 (t, J=7 Hz, 3 H), 1.56 (sxt, J=7 Hz, 2 H), 2.43 (t, J=7 Hz, 2 H), 3.88 (s, 3 H), 4.32 (q, J=7 Hz, 2 H), 7.18 (d, J=6 Hz, 1 H), 7.66 (s, br. 1 H), 7.75 (s, br. 1 H), 7.81 (d, J=6 Hz, 1 H), 8.87 (s, 1 H); MS (m/z): 337 (MH$^+$).

b) 5-(3-Ethoxythiophene-2-yl)-1-methyl-3-n-propyl-6,7-dihydro-1H-pyrazolo-[4,3-d]pyrimidin-7-one (4)

A mixture of 3 (1.15 g, 3.42 mmol), NaOH (284 mg, 7.1 mmol) in ethanol (11 mL) and water (34 mL) was heated at 80° C. for 65 h. After cooling to r.t. a white precipitate was formed. Filtration and drying under vacuum gave 0.625 g of the product. The filtrate was extracted with CH$_2$Cl$_2$, and the organic phase was washed with 1N HCl and brine, dried with MgSO$_4$. Evaporation of the solvent gave additional product; mp: 151–152° C.; $^1$H NMR (CDCl$_3$) δ 1.00 (t, J=7 Hz, 3 H), 1.54 (t, J=7 Hz, 3 H), 1.82 (sxt, J=7 Hz, 2 H), 2.86 (t, J=7 Hz, 2 H), 4.23 (s, 3 H), 4.34 (q, J=7 Hz, 2 H), 6.87 (d, J=6 Hz, 1 H), 7.37 (d, J=6 Hz, 1 H); MS (m/z): 319 (MH$^+$).

c. 5-[3-Ethoxy-5-(4-methylpiperazinylsulfonyl)-thiophene-2-yl]-1-methyl-3-n-propyl-6,7-dihydro-1H-pyrazolo-[4,3-d] pyrimidin-7-one (5) and 5-[3-hydroxy-5-(4-methylpiperazinylsulfonyl)-thiophene-2-yl]-1-methyl-3-n-propyl-6,7-dihydro-1H-pyrazolo-[4,3-d]pyrimidin-7-one (6)

Compound 4 (165 mg, 0.517 mmol) was added to chlorosulfonic acid (0.35 mL, 5.2 mmol) at 0° C. The mixture was stirred under nitrogen at 50° C. for 24 h. Ice was added and the mixture was extracted with a mixture of CH$_2$Cl$_2$/MeOH (9:1), dried with Na$_2$SO$_4$. After evaporation of the solvent, a white solid was obtained which, by NMR analysis contained predominantly 5-(5-chlorosulfonyl-3-ethoxythiophene-2-yl)-1-methyl-3-n-propyl-6,7-dihydro-1H-pyrazolo-[4,3-d]pyrimidin-7-one and a small amount of 5-(5-chlorosulfonyl-3-hydroxythiophene-2-yl)-1-methyl-3-n-propyl-6,7-dihydro-1H-pyrazolo-[4,3-d]pyrimidin-7-one. This white solid (90 mg, 0.456 mmol) was added to a solution of methylpiperazine (137 mg, 1.37 mmol) in methanol (abs. 15 mL) and stirred at rt for 4 days. The solvent was evaporated, and the residue was dissolved in CH$_2$Cl$_2$/MeOH (9:1) and washed with saturated Na$_2$CO$_3$. The aqueous layer was extracted with CH$_2$Cl$_2$/MeOH (9:1). The organic layers were combined and dried with MgSO$_4$. The residue obtained after evaporation of the solvent contained two compounds. Separation and purification was carried out by column chromatography (silica gel). Compound 5 was obtained as a white solid by elution with ethyl acetate; mp: 219–220° C.; $^1$H NMR (DMSO-d$_6$) δ 0.94(t, J=7 Hz, 3H), 1.42(t, J=7 Hz,3 H), 1.74(sxt, J=7 Hz, 2 H), 2.18 (s, 3 H), 2.40 (m, 4 H), 2.76 (t, J=7 Hz, 2 H), 3.35 (m, 4 H), 4.14 (s, 3 H), 4.44 (q, J=7 Hz, 2 H), 7.72 (s, 1 H), 10.79 (br s, 1H); MS (m/z): 481 (MH$^+$). The hydrochloride salt was prepared by adding a solution of HCl in dioxane (4.0 M, 0.2 mL) to a suspension of the free base (6.0 mg) in MeOH (1 mL) and stirring for 1 h. Following removal of the solvents under vacuum a white solid was obtained; mp: 225° C. (dec.).

Compound 6 was obtained as a white solid by elution with 10% methanol in ethyl acetate. The hydrochloride salt was prepared by adding a solution of HCl in dioxane (4.0 M, 0.2 mL) to a suspension of the free base (6.0 mg) in MeOH (1 mL) and stirring for 1h. Following removal of the solvents under vacuum a white solid was obtained; mp: 257° C. (dec.); $^1$H NMR (DMSO-$d_6$) δ 0.95 (t, J=7 Hz, 3 H), 1.75 (t, J=7 Hz, 2 H), 2.49 (s, 3H), 2.70 (m, 6 H), 3.15 (m, 4 H), 4.15 (s, 3 H), 7.61 (s, 1 H), 8.45 (s, 1 H), 10.85 (s, 1 H); MS (m/z) 453 (MH$^+$), 451 (MH$^-$).

EXAMPLE 2

5-(7-Ethoxybenzofuran-2-yl)-1-methyl-3-n-propyl-6,7-dihydro-1H-pyrazolo-[4,3-d]pyrimidin-7-one (7)

a. 4-(7-Ethoxybenzofuran-2-carboxamido)-1-methyl-3-n-propylpyrazole-5-carboxamide From 7-ethoxybenzofuran-2-carbonyl chloride (4.124 g, 20 mmol), 1 (1.82 g, 10 mmol), DMAP (32.5 mg, 0.27 mmol) and Et$_3$N (2.02 g, 20 mmol) in anhydrous CH$_2$Cl$_2$ (65 mL) using the same procedure as for 3 the title compound was obtained as?a white solid; mp: 219–221° C.; $^1$H NMR (DMSO-$d_6$) δ 0.86 (t, J=7 Hz, 3 H), 1.43 (t, J=7 Hz, 3 H), 1.56 (sxt, J=7 Hz, 2 H), 2.42 (t, J=7 Hz, 2 H), 3.91 (s, 3 H), 4.28 (q, J=7 Hz,2 H), 7.10 (d, J=6 Hz, 1 H), 7.26 (t, J=6 Hz, 1 H), 7.35 (d, J=6 Hz, 1 H), 7.50 (s, br. 1 H), 7.71 (s, 1 H), 7.76 (s, br. 1 H); MS (m/z): 371 (MH$^+$).

b. 5-(7-Ethoxybenzofuran-2-yl)-1-methyl-3-n-propyl-6,7-dihydro-1H-pyrazolo-[4,3-d]pyrimidin-7-one (7)

From 4-(7-ethoxybenzofuran-2-carboxamido)-1-methyl-3-n-propylpyrazole-5-carboxamide (281.5 mg, 0.76 mmol) and NaOH (63 mg, 1.573 mmol) in MeOH/H$_2$O (10 mL/6.5 mL) using the procedure for 4 the title compound 7 was obtained as a white solid; mp: 227–229° C.; $^1$H NMR (DMSO-$d_6$) δ 0.98 (t, J=7 Hz, 3 H), 1.46 (t, J=7 Hz, 3 H), 1.78 (sxt, J=7 Hz, 2H), 2.84 (t, J=7 Hz, 2 H), 4.17 (s, 3 H), 4.29 (q, J=7 Hz, 2 H), 7.06 (d, J=6 Hz, 1 H), 7.24 (t, J=6 Hz, 1 H), 7.31 (d, J=6 Hz, 1 H), 7.92 (s, 1 H); MS (m/z): 353 (MH$^+$).

EXAMPLE 3

The sulfonyl chloride precursors to compounds 8, 9, 11, and 32 could be prepared essentially as described in Example 1c with the following provisos:

1) 5-(4-chlorosulfonyl-7-ethoxybenzofuran-2-yl)-1-methyl-3-n-propyl-6,7-dihydro-1H-pyrazolo-[4,3-d]pyrimidin-7-one was obtained by reaction of 5-(7-ethoxybenzofuran-2-yl)-1-methyl-3-n-propyl-6,7-dihydro-1H-pyrazolo-[4,3-d]pyrimidin-7-one (7) with 12 equivalents of chlorosulfonic acid at −7 to 0° C. for 3 h;

2) 5-[4,6-bis-(chlorosulfonyl)-7-ethoxybenzofuran-2-yl]-1-methyl-3-n-propyl-6,7-dihydro-1H-pyrazolo-[4,3-d]pyrimidin-7-one was obtained by reaction of 5-(7-ethoxybenzofuran-2-yl)-1-methyl-3-n-propyl-6,7-dihydro-1H-pyrazolo-[4,3-d]pyrimidin-7-one (7) with 12 equivalents of chlorosulfonic acid at 20° C. for 18 h; and 3) 5-(4-chlorosulfonyl-1-methylpyrrol-2-yl)-1-methyl-3-n-propyl-6,7-dihydro-1H-pyrazolo-[4,3-d]pyrimidin-7-one was obtained by reaction of 5-(1-methylpyrrol-2-yl)-1-methyl-3-n-propyl-6,7-dihydro-1H-pyrazolo-[4,3-d]pyrimidin-7-one (7) with 100 equivalents of chlorosulfonic acid at 20° C. for 4 days.

EXAMPLE 4

As a specific embodiment of an oral composition, 100 mg of the compound 5 of Example 1 is formulated with sufficient finely divided lactose to provide a total amount of 580 to 590 mg to fill a size O hard gel capsule.

Following the procedures described herein, the following compounds in Table 1 were prepared.

TABLE 1

| Compound | R$^3$ | Molecular Ion |
|---|---|---|
| 4 | 2-methyl-3-ethoxythiophene | 319 (M + H) |
| 5 | 5-methyl-4-ethoxy-2-(4-methylpiperazin-1-ylsulfonyl)thiophene | 481 (M + H) |

TABLE 1-continued

| Compound | R³ | Molecular Ion |
|---|---|---|
| 6 | (5-methyl-4-hydroxy-thiophen-2-yl)sulfonyl-(4-methylpiperazine) | 453 (M + H) |
| 7 | 7-ethoxy-2-methylbenzofuran | 353 (M + H) |
| 8 | 7-ethoxy-2-methyl-4-[(4-methylpiperazin-1-yl)sulfonyl]benzofuran | 515 (M + H) |
| 9 | 7-ethoxy-2-methyl-4,6-bis[(4-methylpiperazin-1-yl)sulfonyl]benzofuran | 677 (M + H) |
| 10 | 1,2-dimethylpyrrole | 272 (M + H) |

TABLE 1-continued

| Compound | R³ | Molecular Ion |
|---|---|---|
| 11 | 1,5-dimethyl-pyrrol-3-yl sulfonyl-(4-methylpiperazine) | 434 (M + H) |
| 12 | 5-methyl-4-ethoxy-thiophene-2-sulfonyl-[4-(pyrimidin-2-yl)piperazine] | 545 (M + H) |
| 13 | 5-methyl-4-ethoxy-thiophene-2-sulfonyl-(4-benzylpiperazine) | 557 (M + H) |
| 14 | 5-methyl-4-hydroxy-thiophene-2-sulfonyl-(4-benzylpiperazine) | 529 (M + H) |

TABLE 1-continued

| Compound | R³ | Molecular Ion |
|---|---|---|
| 15 | (4-(pyrimidin-2-yl)piperazin-1-yl)sulfonyl-5-methyl-4-hydroxythiophene | 517 (M + H) |
| 16 | (4-phenylpiperazin-1-yl)sulfonyl-5-methyl-4-ethoxythiophene | 543 (M + H) |
| 17 | (4-phenylpiperazin-1-yl)sulfonyl-5-methyl-4-hydroxythiophene | 515 (M + H) |
| 18 | (4-cinnamylpiperazin-1-yl)sulfonyl-5-methyl-4-ethoxythiophene | 583 (M + H) |

TABLE 1-continued
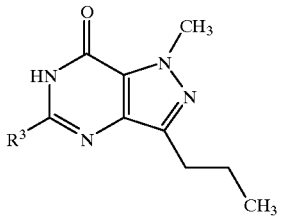
| Compound | R³ | Molecular Ion |
|---|---|---|
| 19 | 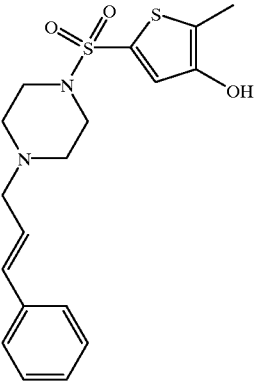 | 555 (M + H) |
| 20 | 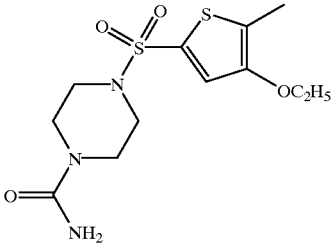 | 509 (M + H) |
| 21 | 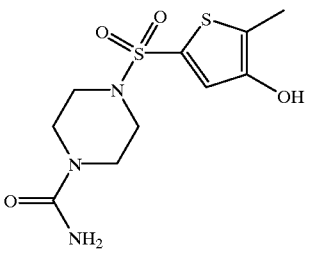 | 481 (M + H) |
| 22 | 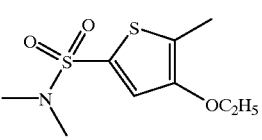 | 426 (M + H) |
| 23 | 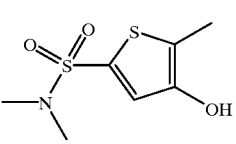 | 398 (M + H) |

TABLE 1-continued
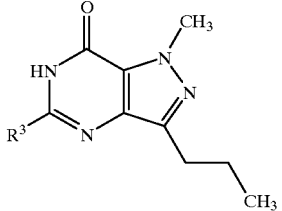
| Compound | R³ | Molecular Ion |
|---|---|---|
| 24 | 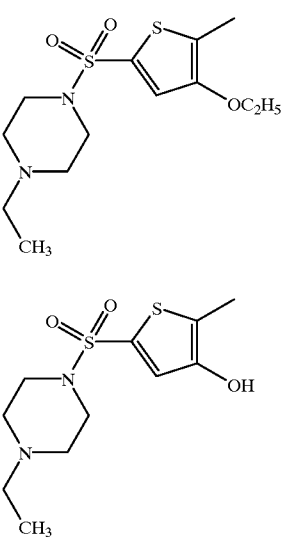 | 495 (M + H) |
| 25 | 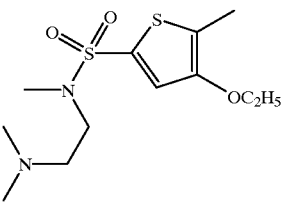 | 467 (M + H) |
| 26 | 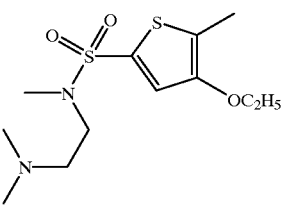 | 483 (M + H) |
| 27 | 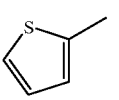 | 455 (M + H) |
| 28 | 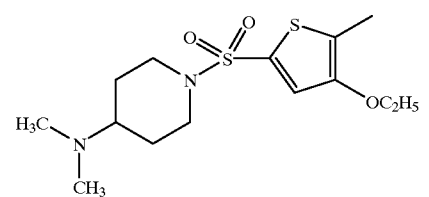 | 275 (M + H) |
| 29 |  | 509 (M + H) |

TABLE 1-continued

[structure of pyrazolopyrimidinone core with R³, CH₃, and propyl substituents]

| Compound | R³ | Molecular Ion |
|---|---|---|
| 30 | 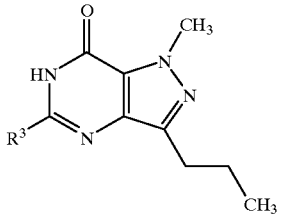 | 549 (M + H) |
| 31 | 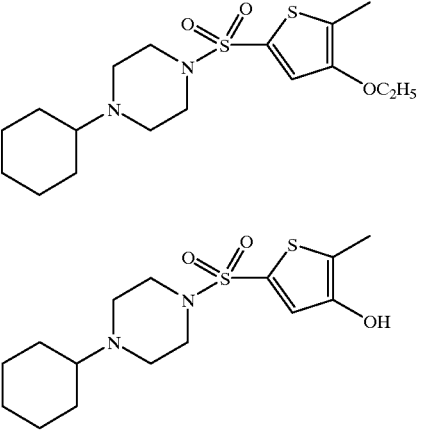 | 521 (M + H) |
| 32 | 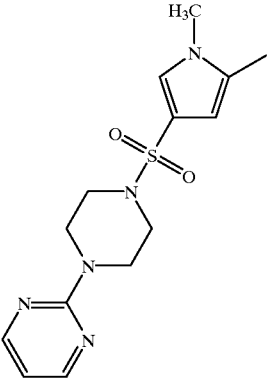 | 496 (M + H) |

EXAMPLE 5

As mentioned previously, it is understood by those skilled in the art that compounds which enhance the release or inhibit the breakdown of cGMP from corpus cavernosum tissue will promote penile erection. Therefore, a method is described to measure the ability of the compounds to increase nitric oxide (NO)-stimulated cGMP levels in penile tissue.

Biological Methods
Measurement of cGMP Levels in Corpus Cavernosum Tissue Rings
Tissue Preparation Male New Zealand White rabbits (2.5 kg) are killed with an overdose of pentobarbitone and their penises excised rapidly. Epidermal and connective tissue is removed and penises cut longitudinally into two equal strips and then laterally to give about 20 segments. The urethra is carefully dissected out and discarded. These segments of corpora cavernosa from all animals are pooled and incubated in Dulbecco's minimum essential medium (MEM) at 37° C. for 1 h with regular changes of medium to allow the tissues to recover from preparative handling.

Effect of Test Compound on cGMP Formation

Tissues are prepared as above; two penile discs for each drug dose are incubated in 200 μL of MEM with various concentrations of test compound and sodium nitroprusside (SNP) added (10 μmol/L final concentration). SNP breaks down spontaneously in aqueous solution to generate NO. After pre-incubation of the tissues with the compounds for 10 min at 37° C., cGMP formation is stimulated with various concentrations of SNP. The tubes are then incubated at 37° C. for a further 30 min and the reaction stopped by adding 200 μL of 1 mol/L perchloric acid. The tissues are ultrasonicated (3×20 s bursts; MSE Soniprep) and the residual tissue pelleted by centrifugation. After centrifugation, aliquots of supernatant are taken and neutralized with 0.5 mol/L $K_3PO_4$. After appropriate dilution in assay buffer, cGMP concentrations are measured by radioimmunoassay (Amersham dual-range $^{125}$I kit) following the manufacturer's instructions. The lower limits of detection are 1 fmol for cGMP assays.

Cyclic Nucleotide Phosphodiesterase (PDE) Assay

PDE Isolation

PDEs were isolated from rabbit tissues according to the protocol described by Boolell et al. in *International Journal of Impotence Research* 1996, 8, 47–52 with minor modifications. Basically, the tissues were homogenized in an ice-cold buffer containing 20 mM HEPES (pH 7.2), 0.25M sucrose, 1 mM EDTA, and 1mM phenylmethyl sulfonylfluoride (PMSF). The homogenates were centrifuged at 100,000 g for 60 minutes at 4° C. The supernatant was filtered through a 0.2 μM filter and loaded on a Pharmacia Mono Q anion exchange column (1 ml bed volume) that was equilibrated with 20 mM HEPES, 1 mM EDTA and 0.5 mM PMSF. After washing out unbound proteins, the enzymes were eluted with a linear gradient of 100–500 mM NaCl in the same buffer (35 to 60 ml total, depending on the tissue). The column was run at the flow rate of 1 ml/min and 1 ml fractions were collected. The fractions comprising various PDE activities were pooled separately and used in later studies.

Measurement of Inhibition of PDE V The PDE assay was carried out essentially as described by Thompson and Appleman in *Biochemistry* 1971, 10, 311–316 with minor modifications. Briefly, the enzyme was assayed in 5 mM $MgCl_2$, 15 mM Tris HCl (pH 7.4), 0.5 mg/ml bovime serum albumin 1 μM cGMP or cAMP, 0.1 μCi [$^3$H]-cGMP or [$^3$H]-cAMP, and 2–10 μl of column elution. The total volume of the assay was 100 μl. The reaction mixture was incubated at 30° C. for 30 minutes. The reaction was stopped by boiling for 1 minute and then cooled on ice. The resulting [$^3$H]5'-mononucleotides were further converted to uncharged [$^3$H]-nucleotides by adding 25 μl 1 mg/ml snake venom (*Ophiophagus hannah*) and incubating at 30° C. for 10 minute. The reaction was stopped by the addition of 1 ml Bio-Rad AG1-X2 resin slurry (1:3). All the charged nucleotides were bound by the resin and only the [$^3$H]-nucleotides remained in the supernatant after centrifuging. An aliquot of 350 μl was taken and counted by liquid scintillation. PDE activity was expressed as pmol cyclic nucleotide hydrolyzed/min/ml of enzyme preparation. Inhibitor studies were carried out in assay buffer with a final concentration of 10% DMSO. Under these conditions, the hydrolysis of substrate did not exceed 15%. The formation of product increased with time and enzyme concentration in a linear fashion.

PDEV inhibitory activities for representative compounds of the present invention are described in Table 2. Data is presented either as the $IC_{50}$ (μM) or as a percent inhibition at a given concentration of test compound.

TABLE 2

| Compound | Activity $IC_{50}$ (μM) | Activity Inhibition % at (conc. μM) |
|---|---|---|
| 4 | 0.47 | |
| 5 | 8 | |
| 6 | 10 | |
| 7 | 0.91 | |
| 8 | 5.4 | |
| 9 | | 6 (20) |
| 10 | 3.5 | |
| 11 | | 31 (10) |
| 12 | 1.2 | |
| 13 | | 46 (20) |

TABLE 2-continued

| Compound | Activity $IC_{50}$ (μM) | Activity Inhibition % at (conc. μM) |
|---|---|---|
| 14 | | 18 (20) |
| 15 | | 13 (20) |
| 16 | | 19 (10) |
| 17 | | 28 (10) |
| 18 | | 44 (10) |
| 19 | | 27 (10) |
| 20 | 0.95 | |
| 21 | | 30 (10) |
| 22 | 1.4 | |
| 23 | | 30 (10) |
| 24 | 2.3 | |
| 25 | | 26 (10) |
| 26 | 4.9 | |
| 27 | | 32 (10) |
| 28 | 1.6 | |
| 29 | 8.3 | |
| 30 | | 33 (10) |
| 31 | | 31 (10) |
| 32 | | 31 (10) |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of formula (I)

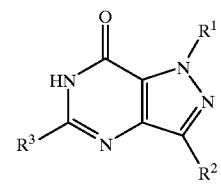

(I)

wherein $R^1$ and $R^2$ are each independently selected from hydrogen or $C_1$–$C_6$ alkyl;

$R^3$ is selected from

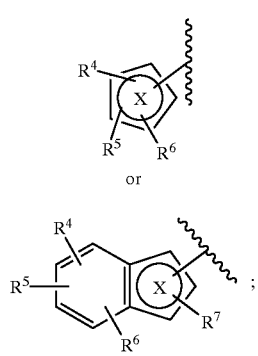

is a five membered heteroaromatic ring which consists of carbon atoms and from one to three heteroatoms selected from N, O or S;

$R^4$, $R^5$, $R^6$ and $R^7$ are each independently selected from hydrogen, $C_1$–$C_6$ alkyl, fluorinated $C_1$–$C_6$ alkyl, cyano, (hydroxy)$C_1$–$C_6$ alkyl, $C_1$–$C_6$ alkoxy, fluorinated $C_1$–$C_6$ alkoxy, $C_1$–$C_6$ alkanoyl, halogen, hydroxy, $C_1$–$C_6$ alkyl-$NR^8R^9$, $NR^8R^9$, $CONR^8R^9$ or $SO_2NR^8R^9$;

$R^8$ is selected from hydrogen or $C_1$–$C_6$ alkyl, $R^9$ is selected from hydrogen, $C_1$–$C_6$ alkyl, or $C_1$–$C_6$ alkyl-$NR^{13}R^{14}$, or $R^8$ and $R^9$ together with the nitrogen to which they are attached form an unsubstituted or substituted pyrrolidinyl, piperidinyl, morpholinyl or 4-N($R^{10}$)-piperazinyl group wherein the substituent is selected from $C_1$–$C_6$ alkyl, $C_1$–$C_6$ alkoxy, $NR^{11}R^{12}$ or $CONR^{11}R^{12}$;

$R^{10}$ is selected from hydrogen, $C_1$–$C_6$ alkyl, $C_3$–$C_6$ cycloalkyl, (hydroxy)$C_1$–$C_6$ alkyl, aryl, heteroaryl, aralkyl, aralkenyl or $C(O)NH_2$; and $R^{11}$ and $R^{12}$ are each independently selected from hydrogen, $C_1$–$C_6$ alkyl, (hydroxy)$C_1$–$C_6$ alkyl or ($C_1$–$C_6$ alkoxy)$C_1$–$C_6$ alkyl; and $R^{13}$ and $R^{14}$ are each independently selected from hydrogen or $C_1$–$C_6$ alkyl, or $R^{13}$ and $R^{14}$ together with the nitrogen to which they are attached form an unsubstituted or substituted pyrrolidinyl, piperidinyl or morpholinyl group;

provided that when $R^3$ is

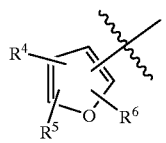

and $R^5$ and $R^6$ are both hydrogen, then $R^4$ is selected from hydrogen, $C_1$–$C_6$ alkyl, fluorinated $C_1$–$C_6$ alkyl, cyano, (hydroxy)$C_2$–$C_6$ alkyl, $C_1$–$C_6$ alkoxy, fluorinated $C_1$–$C_6$ alkoxy, $C_1$–$C_6$ alkanoyl, halogen, hydroxy, $C_1$–$C_6$ alkyl-$NR^8R^9$, $NR^8R^9$, $CONR^8R^9$ or $SO_2NR^8R^9$;

and pharmaceutically acceptable salts thereof.

2. The compound of claim 1, wherein $R^1$ and $R^2$ are each independently selected from hydrogen and $C_1$–$C_4$ alkyl;

$R_3$ is selected from

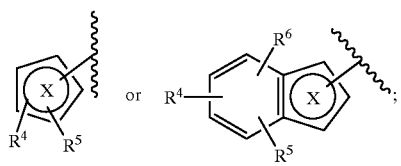

is a five membered heteroaromatic ring selected from pyrrolyl, furanyl, thienyl, or imidazolyl;

$R^4$ and $R^6$ are each independently selected from hydrogen, $C_1$–$C_4$ alkyl, fluorinated $C_1$–$C_4$ alkyl, cyano, (hydroxy)$C_1$–$C_4$ alkyl, $C_1$–$C_4$ alkoxy, fluorinated $C_1$–$C_4$ alkoxy, $C_1$–$C_4$ alkanoyl, halogen, hydroxy, $C_1$–$C_4$ alkyl-$NR^8R^9$, $NR^8R^9$, $CONR^8R^9$ or $SO_2NR^8R^9$;

$R^5$ is selected from hydrogen, $C_1$–$C_4$ alkyl or $C_1$–$C_4$ alkoxy;

$R^8$ is selected from hydrogen or $C_1$–$C_4$ alkyl, $R^9$ is selected from hydrogen, $C_1$–$C_4$ alkyl, or $C_1$–$C_4$ alkyl-$NR^{13}R^{14}$, or $R^8$ and $R^9$ together with the nitrogen to which they are attached form an unsubstituted or substituted pyrrolidinyl, piperidinyl, morpholinyl or 4-N($R^{10}$)-piperazinyl group wherein the substituent is selected from $C_1$–$C_4$ alkyl, $C_1$–$C_4$ alkoxy, $NR^{11}R^{12}$ or $CONR^{11}R^{12}$; and $R^{10}$ is selected from hydrogen, $C_1$–$C_4$ alkyl, (hydroxy) $C_1$–$C_4$ alkyl, aryl, heteroaryl, ar($C_1$–$C_4$)alkyl, ar($C_1$–$C_4$)alkenyl or $C(O)NH_2$;

provided that when $R^3$ is

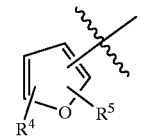

and $R^5$ is hydrogen, then $R^4$ is selected from hydrogen, $C_1$–$C_4$ alkyl, fluorinated $C_1$–$C_4$ alkyl, cyano, (hydroxy) $C_2$–$C_4$ alkyl, $C_1$–$C_4$ alkoxy, fluorinated $C_{1-C4}$ alkoxy, $C_1$–$C_4$ alkanoyl, halogen, hydroxy, $C_1$–$C_4$ alkyl-$NR^8R^9$, $NR^8R^9$, $CONR^8R^9$ or $SO_2NR^8R^9$;

and pharmaceutically acceptable salts thereof.

3. The compound of claim 2 selected from

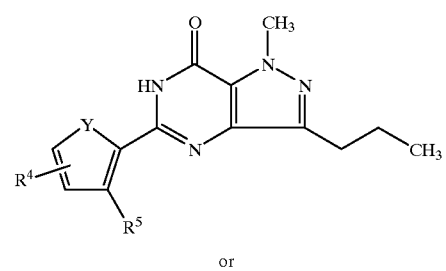

or

-continued

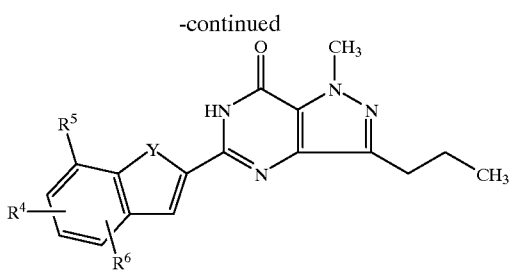

wherein Y is selected from O, S or N—$R^{15}$ where $R^{15}$ is selected from hydrogen and $C_1$–$C_4$ alkyl;

and pharmaceutically acceptable salts thereof.

4. The compound of claim 1, wherein $R^{10}$ is selected from hydrogen, $C_1$–$C_6$ alkyl, (hydroxy) $C_1$–$C_6$ alkyl, aryl, heteroaryl, aralkyl, aralkenyl or $C(O)NH_2$;

and pharmaceutically acceptable salts thereof.

5. A pharmaceutical composition comprising a pharmaceutically acceptable carrier and a compound of claim 1.

6. A pharmaceutical composition made by mixing a compound of claim 1 and a pharmaceutically acceptable carrier.

7. A process for making a pharmaceutical composition comprising mixing a compound of claim 1 and a pharmaceutically acceptable carrier.

8. A method of treating sexual dysfunction in a subject in need thereof comprising administering to the subject a therapeutically effective amount of the compound of claim 1.

9. The method of treating sexual dysfunction of claim 8, wherein the sexual dysfunction is male erectile dysfunction.

10. A method of treating sexual dysfunction in a subject in need thereof comprising administering to the subject a therapeutically effective amount of the composition of claim 5.

11. The method of treating sexual dysfunction of claim 10, wherein the sexual dysfunction is male erectile dysfunction.

12. A method of treating impotence in a male subject in need thereof comprising administering to the subject a therapeutically effective amount of the compound of claim 1.

13. A method of treating impotence in a male subject in need thereof comprising administering to the subject a therapeutically effective amount of the composition of claim 5.

14. A method of treating a condition selected from the group consisting of heart failure, pulmonary hypertension, and angina in a subject in need thereof comprising administering to the subject a therapeutically effective amount of the compound of claim 1.

15. A method of treating a condition selected from the group consisting of heart failure, pulmonary hypertension, and angina in a subject in need thereof comprising administering to the subject a therapeutically effective amount of the composition of claim 5.

* * * * *

UNITED STATES PATENT AND TRADEMARK OFFICE
CERTIFICATE OF CORRECTION

PATENT NO.    : 6,077,841
DATED         : June 20, 2000
INVENTOR(S)   : Zhihua Sui et al.

It is certified that error appears in the above-identified patent and that said Letters Patent is hereby corrected as shown below:

<u>Title page,</u>
Item [73], Assignee should read -- Ortho-McNeil Pharmaceutical, Inc., Raritan, NJ --

Signed and Sealed this

Ninth Day of July, 2002

*Attest:*

*Attesting Officer*

JAMES E. ROGAN
*Director of the United States Patent and Trademark Office*